United States Patent
Kung et al.

(10) Patent No.: US 10,369,384 B2
(45) Date of Patent: Aug. 6, 2019

(54) GRID CALIBRATION SYSTEM FOR INTERVENTIONAL PROCEDURES

(71) Applicant: KONINKLIJKE PHILIPS N.V., Eindhoven (NL)

(72) Inventors: Cynthia Ming-Fu Kung, New York, NY (US); Shyam Bharat, Arlington, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 187 days.

(21) Appl. No.: 15/324,765

(22) PCT Filed: Jul. 9, 2015

(86) PCT No.: PCT/IB2015/055201
§ 371 (c)(1),
(2) Date: Jan. 9, 2017

(87) PCT Pub. No.: WO2016/009312
PCT Pub. Date: Jan. 21, 2016

(65) Prior Publication Data
US 2017/0203128 A1 Jul. 20, 2017

Related U.S. Application Data

(60) Provisional application No. 62/023,977, filed on Jul. 14, 2014.

(51) Int. Cl.
*A61N 5/10* (2006.01)
*A61B 8/12* (2006.01)
(Continued)

(52) U.S. Cl.
CPC ............ *A61N 5/1075* (2013.01); *A61B 8/12* (2013.01); *A61B 8/4209* (2013.01);
(Continued)

(58) Field of Classification Search
CPC .............. A61N 5/1001; A61N 5/1007; A61N 2005/1012; A61N 2005/1023;
(Continued)

(56) References Cited

U.S. PATENT DOCUMENTS 6,438,401 B1   8/2002  Cheng et al.
2012/0302890 A1* 11/2012 Strong ................. A61N 5/1027
                                                       600/459

(Continued)

FOREIGN PATENT DOCUMENTS

JP        2007000226 A      1/2007

OTHER PUBLICATIONS

Chen, T.K. et al., "Automated intraoperative calibration for prostate cancer brachytherapy", Med. Phys. 38(11), Nov. 2011, pp. 6285-6299.

*Primary Examiner* — Carrie R Dorna (57) ABSTRACT

A grid calibration system employing interventional equipment including one or more interventional tools (23), a grid (22) having a hole matrix for supporting and guiding the interventional tool(s) (23) within a calibration area, and an imaging device (24) positioned relative to the grid (22) for generating a tool image illustrative of the interventional tool(s) (23) within the calibration area. The grid calibration system further employs a grid calibration workstation (40) for displaying any alignment adjustments to the relative positioning of the grid (22) and the imaging device (24) as derived from an image registration of the tool image and a virtual grid having a point matrix representative of the hole matrix of the grid.

15 Claims, 5 Drawing Sheets

(51) Int. Cl.
*A61B 8/00* (2006.01)
*A61B 34/20* (2016.01)
*A61B 17/00* (2006.01)

(52) U.S. Cl.
CPC ............ *A61B 8/4263* (2013.01); *A61B 34/20* (2016.02); *A61N 5/1007* (2013.01); *A61N 5/1027* (2013.01); *A61B 8/587* (2013.01); *A61B 2017/00274* (2013.01); *A61B 2034/2051* (2016.02); *A61N 2005/1012* (2013.01)

(58) Field of Classification Search
CPC ........... A61N 2005/1024; G01D 18/00; G01D 18/002; G01D 18/004; G01D 18/006; G01D 18/008
See application file for complete search history.

(56) References Cited

U.S. PATENT DOCUMENTS

| | | |
|---|---|---|
| 2014/0121501 A1 | 5/2014 | Fichtinger et al. |
| 2015/0051861 A1 | 2/2015 | Kruecker et al. |
| 2015/0216619 A1 | 8/2015 | Kruecker et al. |
| 2016/0000519 A1 | 1/2016 | Marvast |

* cited by examiner

GRID CALIBRATION SYSTEM FOR INTERVENTIONAL PROCEDURES

CROSS-REFERENCE TO PRIOR APPLICATIONS

This application is the U.S. National Phase application under 35 U.S.C. § 371 of International Application Serial No. PCT/IB2015/055201, filed on Jul. 9, 2015, which claims the benefit of U.S. Application Ser. No. 62/023,977, filed on Jul. 14, 2014. These applications are hereby incorporated by reference herein.

The present invention generally relates to a grid calibration system incorporated within an interventional procedure (e.g., a prostate brachytherapy procedure). The present invention specifically relates to a calibration of a grid (also known as a template) for supporting and guiding interventional tools (e.g., catheters, needles, etc.) within an anatomical region of interest relative to an imaging plane of an ultrasound probe during an interventional procedure.

Prostate cancer is the most common non-skin related cancer and the second leading cause of cancer death in American men. Affecting one in six (6) men, an estimated 238,000 new cases of prostate cancer will be diagnosed in 2013, 30,000 of which will be fatal. Brachytherapy, with both high-dose-rate ("HDR") and low-dose-rate ("LDR") procedures, is a common radiotherapy used to treat prostate cancer. Generally, HDR prostate brachytherapy involves a transperineal insertion of ten (10)-twenty (20) catheters into the prostate followed by a temporary sequential insertion of a radioactive source into each of these catheters using a remote afterloader. By comparison, LDR prostate brachytherapy involves a permanent implantation within the prostate of approximately 100 radioactive seeds delivered through numerous needles inserted in the prostate. For both HDR and LDR prostate brachytherapy procedures as well as other prostate procedures (e.g., transperineal prostate biopsy), the catheters or the needles are typically inserted through a grid/template that is positioned against the perineum to provide support and guidance for an even distribution and securing of the catheters or the needles once they are inserted into the prostate.

Figure 1:
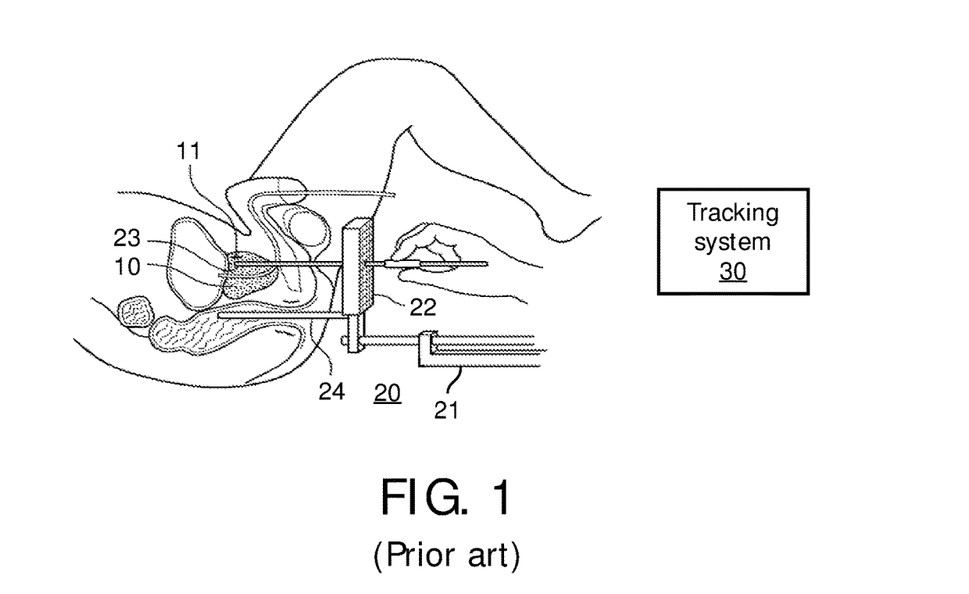
FIG. 1 illustrates an exemplary prostate brachytherapy procedure as known in the art.

For example, FIG. 1 illustrates a typical prostate brachytherapy equipment setup 20 involving a catheter/needle 23. Specifically, the exemplary prostate brachytherapy procedure is implemented under an ultrasound guidance using a transrectal ultrasound ("TRUS") probe 24 positioned together with a grid/template 22 on a stepper 21 for providing stability to the whole setup 20 as grid/template 22 is held in place and TRUS probe 24 is allowed to translate and rotate in and about an axial direction that is roughly perpendicular to grid/template 22. Catheter/needle 23 is either positioned according to a predetermined plan, or retroactively identified in an ultrasound image along with segmentations of a prostate 10 and surrounding organs whereby a relative geometry between catheter/needle 23 and the organ segmentations is used to determine a dose distribution of radioactive seed(s) (e.g., a radioactive seed 11) and a specific treatment plan.

A manual identification of catheter/needle 23 via echo flashes in an ultrasound image is prone to error due to factors such as poor image quality, obscuring structures, and operator experience. A tracking system 30 (e.g., an electromagnetic ("EM") tracking system or an optical tracking system) has recently been proposed for HDR and LDR prostate brachytherapy procedures to overcome these limitations and improve overall accuracy. More particularly as related to an EM tracking system, EM sensors (not shown) are integrated into both catheter/needle 23 and TRUS probe 24 for an accurate spatial localization within an EM coordinate system of catheter/needle 23 and TRUS probe 24 with respect to prostate 10 and the surrounding anatomical region of interest. While grid/template 22 may be also integrated with a tracking sensor, in cases whereby grid/template 22 is not integrated with a tracking sensor, alternate methods of locating grid/template 22 within the EM coordinate system may involve an EM grid calibration performed in which a tracked catheter/needle 23 is inserted into various locations of the hole matrix to create a mapping of an entirety of grid/template 22. This localization of the hole matrix of grid/template 22 within the EM coordinate system is known as the "EM grid."

Figure 2:
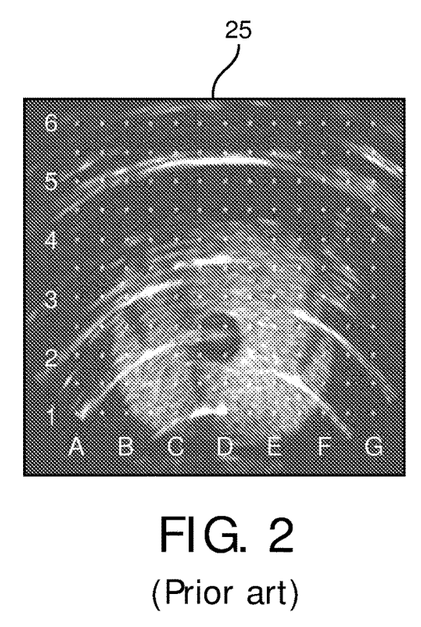
FIGS. 2 and 3 illustrate exemplary ultrasound images having virtual grid overlays as known in the art.
Figure 3:
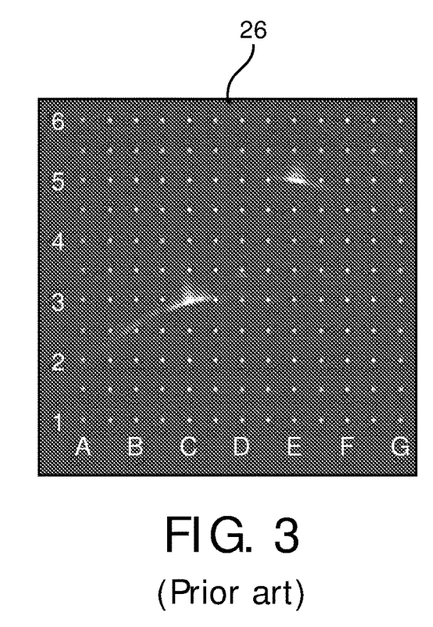

During the prostate brachytherapy procedures, certain models of an ultrasound scanner are equipped with a feature to overlay a "virtual grid" over the ultrasound image from TRUS probe 24 to provide a visual aid for the alignment of the hole matrix of grid/template 22, such as, for example, an overlay of a virtual grid of white dots over an ultrasound image 25 as shown in FIG. 2. This is meant to serve as a projection of the hole matrix of grid/template 22 on an image plane (not shown) of TRUS probe 24. As exemplary shown in FIG. 2, the virtual grid is simply an overlay onto ultrasound image 25 of M×N grid points with a selected spacing (typically 5 mm or 10 mm) identical or equivalent to the M×N holes and spacing of hole matrix of grid/template 22. For accurate tracking purposes, an alignment of the hole matrix grid/template 22 to the virtual grid is manually performed by an operator. This calibration for setup 20 will typically be done occasionally (e.g., daily/weekly/monthly) by inserting catheters/needles through the hole matrix of grid/template 22 in a water tank and adjusting a physical position of grid/template 22 as necessary such that the virtual grid overlay coincides to the highest extent possible with the hole matrix of grid/template 22 as represented by echo flashes of the tools within the image plane of TRUS probe 24. FIG. 3 shows two (2) ultrasound echoes corresponding to the C3 and E5 locations in an ultrasound image 26 representative of a true alignment of the hole matrix of grid/template 22 to the virtual grid. However, in practice, such a true alignment is rarely achieved and/or maintained over the course of numerous prostate brachytherapy procedures.

Currently, the process of grid calibration to align the hole matrix of grid/template 22 with an ultrasound virtual grid is done manually and involves subjective visual confirmation of alignment by the operator. More specifically, a translation of grid/template 22 in a vertical direction and/or a horizontal direction as well as a rotation of TRUS probe 24 are adjusted on a "trial and error" basis, which can be time consuming and subject to inter-operator variability. Thus, a problem in the art is the difficulty in determining an optimal combination of grid translation(s) and/or probe rotation required for accurate positioning of grid/template 22 and TRUS probe 24 relative to stepper 21 to thereby align the hole matrix of grid-template 22 to the virtual grid overlay as shown in FIG. 3.

The present invention proposes an automated quality assurance method to aid in the calibration of a grid/template (e.g., grid/template 22 shown in FIG. 1) and also provides a quantification of alignment error(s). The present invention involves the use of an image identification method to automatically detect the location of the tools flashes and projected ultrasound grid points via the virtual grid. From this information, precise translation and/or rotation parameters needed for accurate alignment of the grid/template to the virtual grid can be calculated and displayed to the operator. The present invention may also be utilized to determine a fit error between the grid/template and the virtual grid, or any other type of external grid reference (e.g., tracking system 30 shown in FIG. 1).

One form of the present invention is a grid calibration system employing interventional equipment including one or more interventional tools (e.g., catheter(s) or needle(s), a grid having a hole matrix for supporting and guiding the interventional tool(s) within a calibration area, and an ultrasound probe positioned relative to the grid for generating a tool image illustrative of the interventional tool(s) within the calibration area.

The grid calibration system further employs a grid calibration workstation for displaying any alignment adjustments to the relative positioning of the grid and the ultrasound probe as derived from an image registration of the tool image and a virtual grid having a point matrix representative of the hole matrix of the grid. The alignment adjustments may include a horizontal translational adjustment of the grid relative to the ultrasound probe, a vertical translational adjustment of the grid relative to the ultrasound probe and/or a rotational adjustment of the probe relative to the grid.

For translational adjustments only, preferably two (2) or more interventional tools are utilized for generating the tool image.

For rotational adjustment, preferably three (3) or more interventional tools are utilized for generating the tool image.

The grid calibration workstation may additionally display an alignment fit error (e.g., least square) of the tool image to the virtual grid. The alignment fit error may be applied against a threshold indicative of whether alignment fit error is acceptable or unacceptable for a corresponding interventional procedure (e.g., a HDR or LDR prostate brachytherapy procedure).

The interventional equipment may further include a tracking system (e.g., an EM tracking system) positioned relative to the grid and having sensors integrated with the interventional tool(s) and/or the grid for generating a tracking grid representative of the hole matrix of the grid. With a generation of the tracking grid, the grid calibration workstation may additionally display a virtual tracking fit error (e.g., least square) of the tracking grid to the virtual grid and/or an image tracking fit error (e.g., least square) of the tracking grid to the tool image. The tracking fit error(s) may be applied against threshold(s) indicative of whether a tracking accuracy of the EM tracking system is acceptable or unacceptable for the corresponding interventional procedure.

The foregoing form and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 4:
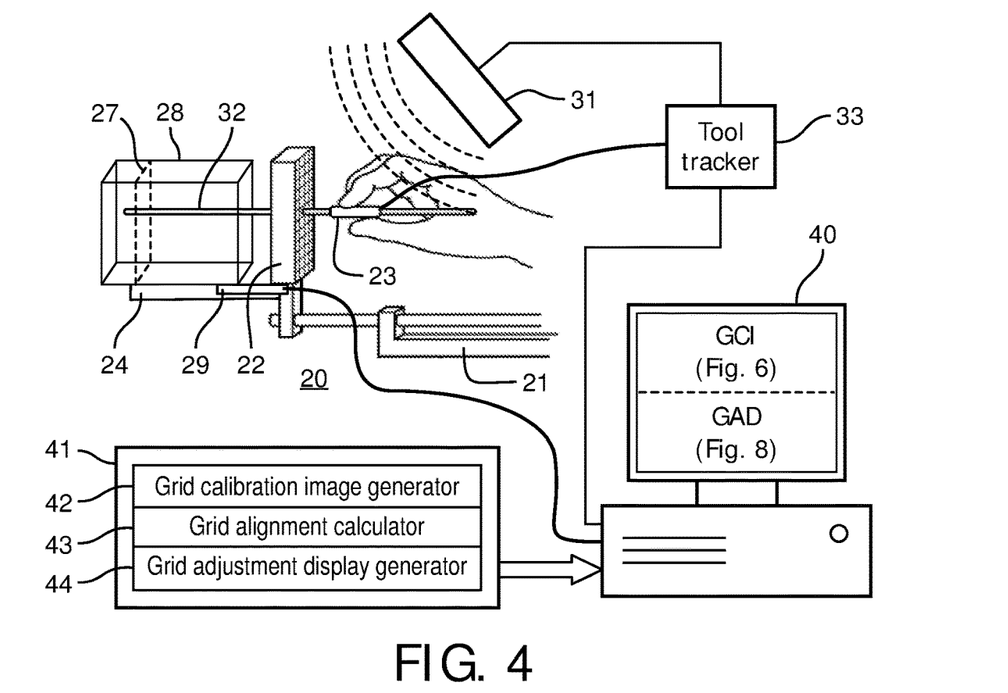
FIG. 4 illustrates an exemplary embodiment of a grid calibration system in accordance with the present invention.
Figure 5:
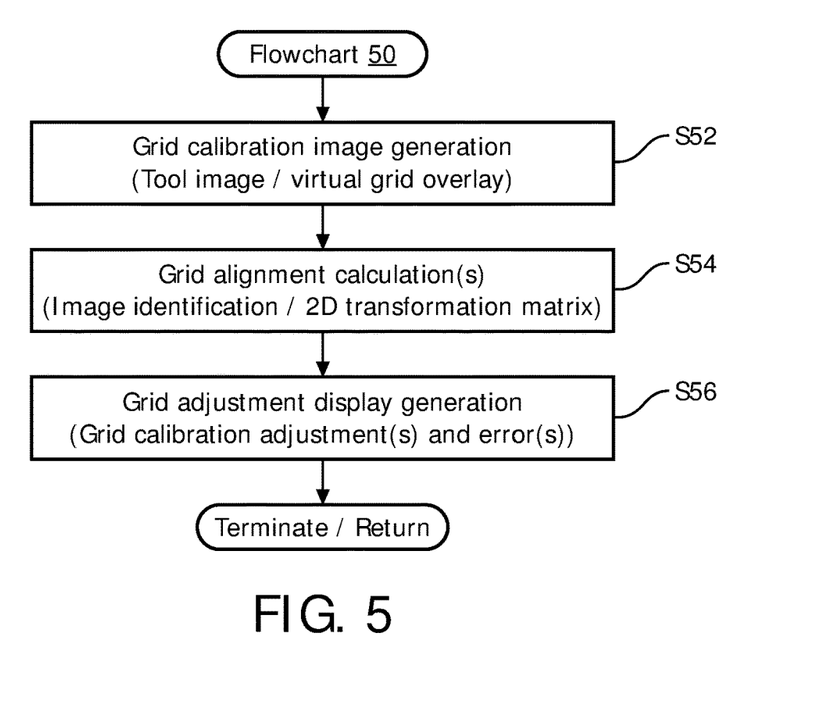
FIG. 5 illustrates a flowchart representative of an exemplary embodiment of an a grid calibration method in accordance with present invention.

To facilitate an understanding of the present invention, exemplary embodiments of a grid calibration system and method of the present invention as respectively shown in FIGS. 4 and 5 in the context of an ultrasound imaging of an interventional tool as tracked by an EM tracking system will be provided herein. From the description of the exemplary embodiments, those having ordinary skill in the art will appreciate how to apply the operating principles of the present invention to an implementation of a grid calibration system/method for (1) for a base calibration method exclusive of a tracking grid, (2) for a tracking calibration method inclusive of a tracking grid, (3) a variety of types of interventional tools and grids for either calibration method, (4) alternative imaging devices for either calibration method and (5) alternative tracking systems for the tracking calibration method.

Referring to FIG. 4, interventional equipment 20 of FIG. 1 further employs a water tank/phantom 28 positioned on a support 29 of stepper 21 as known in the art for facilitating an ultrasound image 27 of water tank/phantom 28. The EM tracking system employs an EM field generator 31, an EM sensor 32 integrated with interventional tool 23, an EM sensor (not shown) integrated with TRUS probe 24, an optional EM sensor integrated with grid/template 22, and a tool tracker 33 as known in the art.

Generally in operation, one (1) or more interventional tools 23 are inserted through various holes of the hole matrix of grid/template 22 whereby interventional tool(s) 23 are visible as echo flash(es) in ultrasound image 27. From an imaging of preferably two (2) or more interventional tools 23, grid calibration translational adjustments are displayed in terms of (1) a translation of grid/template 22 in a vertical direction for a height adjustment of grid/template 22 relative to TRUS probe 24 and (2) a translation of grid/template 22 in a horizontal direction for a transverse adjustment of grid/template 22 relative to TRUS probe 24. From an imaging of preferably three (3) or more interventional tools 23, a grid calibration rotational adjustment is displayed in terms of a rotation of TRUS probe 24 in a clockwise or counterclockwise direction for angular adjustment of ultrasound image 27 relative to grid/template 22. To this end, a grid calibration workstation 40 employs a modular network 41 structurally configured as hardware, software, firmware and/or circuitry of workstation 40.

Specifically, modular network 41 includes a grid calibration image ("GCI") generator 42 for generating a grid calibration image having a virtual grid overlay on ultrasound image 27 of interventional tools 23 as inserted through the hole matrix of grid/template 22 (hereinafter "tool image 27"), such as, for example, GCI 26 shown in FIG. 3.

In practice, the virtual grid overlay is any form of a M×N matrix of grid points, preferably M≥2 and N≥2. In one embodiment, GCI generator 42 provides an interface for a user of workstation 40 to select among a variety of preset virtual grids or to specify a particular virtual grid, particularly when a point number and spacing of preset virtual grid is not identical or equivalent to the hole matrix of grid/template 22.

Modular network 41 further includes a grid alignment calculator 43 for calculating the aforementioned translational and/or rotational grid calibration adjustments(s) of grid/template 22 and TRUS probe 24 to achieve a "best fit" between the virtual grid overlay and tool image 27. Additionally, grid alignment calculator 43 may calculate (1) an "adjustment fit error" between the virtual grid overlay and tool image 27, (2) a "virtual tracking fit error" between the virtual grid overlay and an EM grid representative of an EM localization of the hole matrix of grid/template 22 as known in the art and/or (3) an "image tracking fit error" between the tool image and an EM grid representative of an EM localization of the hole matrix of grid/template 22 as known in the art.

Modular network 41 further includes a grid adjustment display generator 44 for generating a real-time display of the translational and/or rotational grid calibration adjustment(s) as grid/template 22 is being translated and/or TRUS probe 24 is being rotated to achieve an alignment of the hole matrix of grid/template 22 and the virtual grid overlay. Additionally, if calculated, grid adjustment display generator 44 also generates a real-time display of the adjustment fit error between the virtual grid overlay and tool image 27, the virtual tracking fit error between the virtual grid overlay and the EM grid and/or the image tracking fit error between the tool image and the EM grid.

To further facilitate an understanding of the present invention, a flowchart 50 representative of a grid calibration method of the present invention as executed by flowchart 40 will now be described herein. While the description of flowchart 50 will be in the context of utilizing six (6) interventional tools for grid calibration purposes, those having ordinary skill in the art will appreciate any number of interventional tools may be used for such grid calibration purposes, preferably between three (3) and seven (7) interventional tools.

Referring to FIG. 5, a stage S52 of flowchart 50 encompasses a generation by workstation 40 of a grid calibration image having a virtual grid overlay on a tool image.

Figure 6:
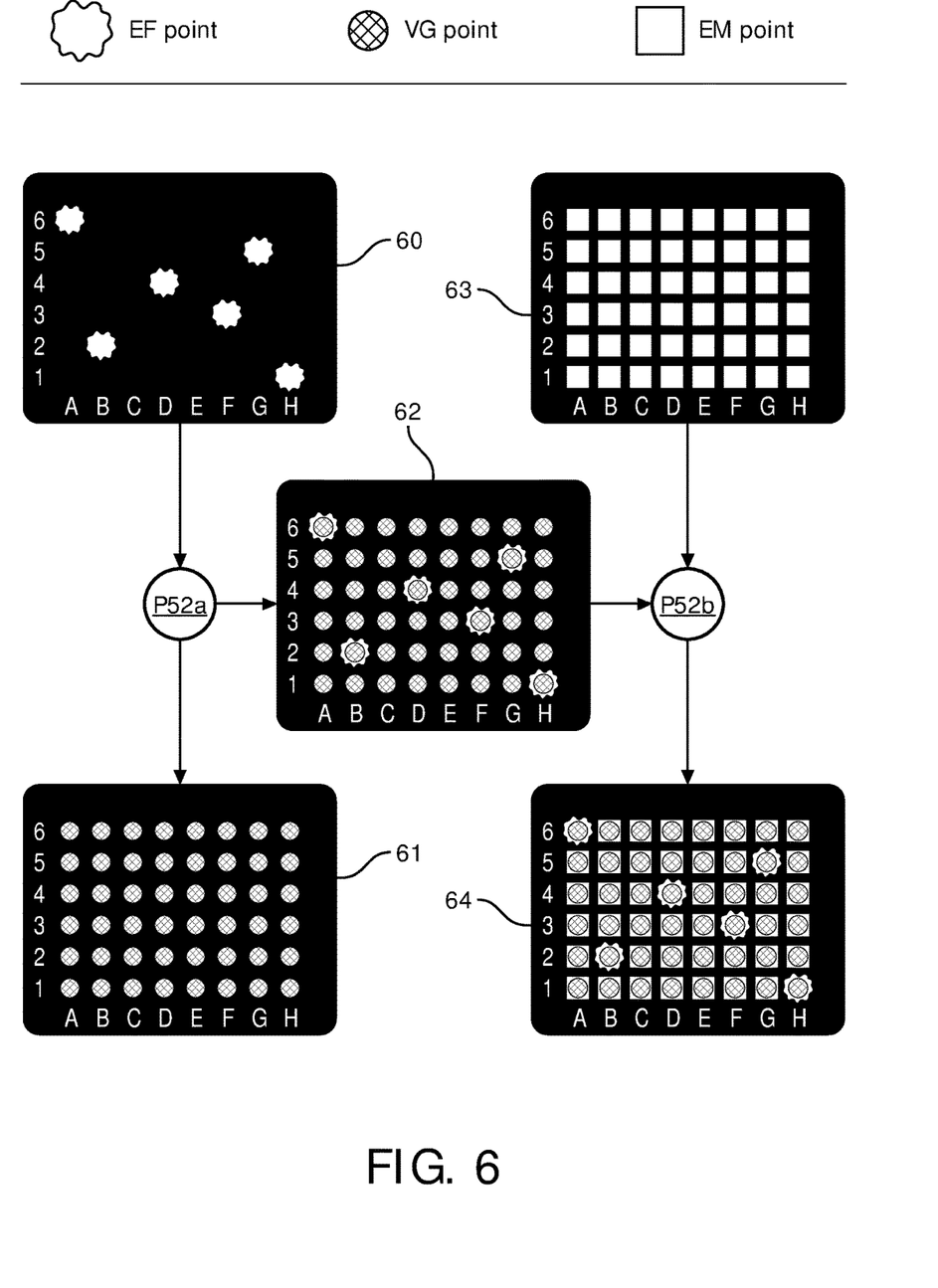
FIG. 6 illustrates exemplary grid calibration images as generated by an exemplary execution of the flowchart shown in FIG. 5 by the system shown in FIG. 4.

In one embodiment as exemplary shown in FIG. 6, TRUS probe 24 is operated to generate a tool image 60 having six (6) echo flashes ("EF") points from six (6) interventional tools 23 inserted within a six (6) row×eight (8) column hole matrix of grid/template 22 at locations A6, B2, D4, F3, G5, and H1. During a phase P52a of stage S52, generator 42 overlays a virtual grid 61 onto tool image 60 to display a grid calibration image 62. Optionally based on EM tracking of the six (6) interventional tools 23 and/or grid/template 22, during a phase P52b of stage S52, generator 42 overlays a six (6) row×eight (8) column EM grid 63 of EM points onto grid calibration image 62 to form a grid calibration image 64. This embodiment is beneficial when an alignment of tool image 60 and virtual grid 61 may be off by more than one (1) row spacing and/or by more than one (1) column spacing whereby the EM coordinates of the six (6) interventional tools may utilized to detect the offset.

Referring back to FIG. 5, a stage S54 of flowchart 50 encompasses a calculation of grid calibration adjustment(s) to align tool image 60 and virtual grid 61 to a greatest degree possible.

Figure 7:
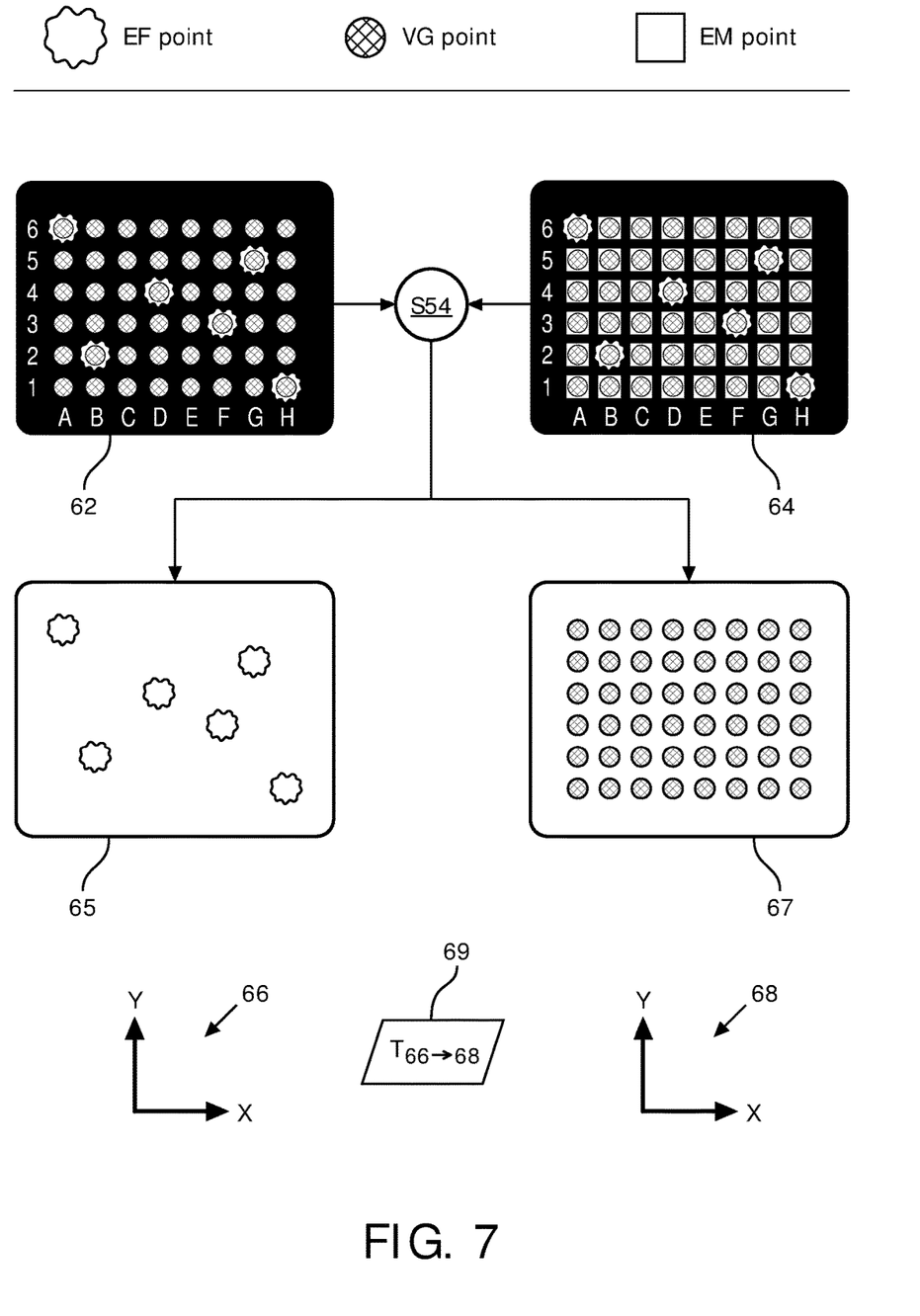
FIG. 7 illustrates an exemplary transformation matrix calculation as generated by an exemplary execution of the flowchart shown in FIG. 5 by the system shown in FIG. 4.

In one embodiment as exemplary shown in FIG. 7, calculator 43 (FIG. 4) executes an image identification/segmentation algorithm of GCI 62 or GCI 64 as known in the art to generate flash image 65 and point matrix image 67. Subsequently, calculator 43 calculates a two-dimensional ("2D") transformation matrix 69 of a 2D coordinate system 66 associated with flash image 65 to a 2D coordinate system 68 associated with point matrix image 67. Transformation matrix 69 provides for any translational and/or rotational values needed to adjust grid/template 22 and/or TRUS probe 24 from current translational/rotational positions to a "best fit" for aligning tool image 60 and virtual grid 61. Additionally, once the 'best fit' is achieved, transformation matrix 69 facilitates a calculation of an adjustment fit error (e.g., least-squares) between tool image 60 and virtual grid 61 and a virtual tracking fit error between EM grid 63 and virtual grid 61, and optionally a tool tracking fit error between tool image 60 and EM grid 63. As previously stated herein, the tracking fit error(s) at the current location of grid/template 22 will indicate the fidelity of EM grid 63 and therefore, whether a new EM grid calibration needs to be performed at the current grid location.

Referring back to FIG. 5, a stage S56 of flowchart 50 encompasses a display of the calculated grid adjustments needed, in real-time, as grid/template 22 and/or TRUS probe 24 is adjusted to achieve the "best fit".

Figure 8:
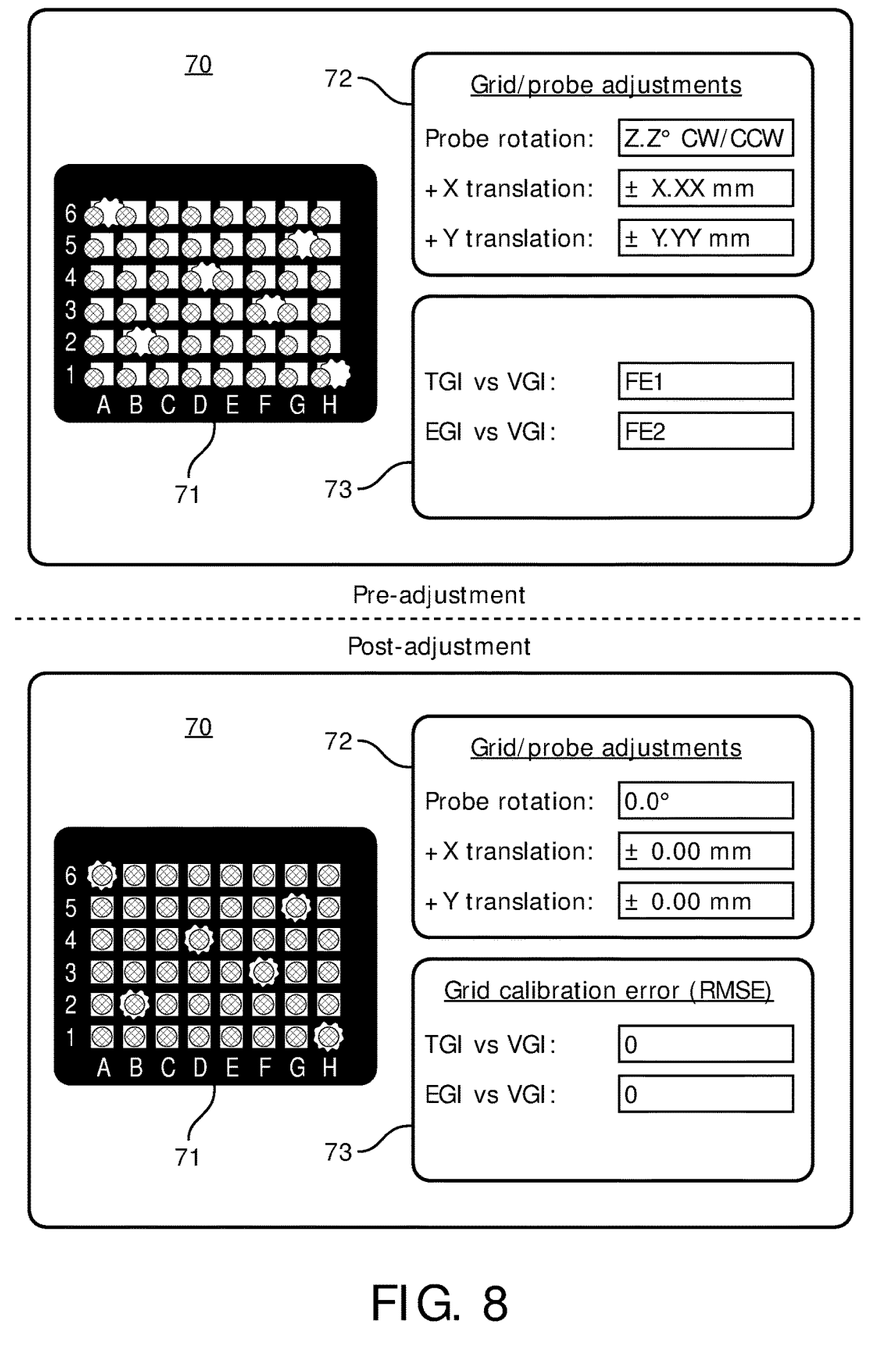
FIG. 8 illustrates exemplary graphical use interfaces as generated by an exemplary execution of the flowchart shown in FIG. 5 by the system shown in FIG. 4.

In one embodiment as exemplarily shown in FIG. 8, a user interface 70 displays a dynamic grid calibration image 71, a grid/probe adjustment readout 72 and a grid calibration error 73.

Dynamic grid calibration image 71 will highlight any adjustments of grid/template 22 and/or TRUS probe 24, such as, for example, a misalignment of image 71 during a pre-adjustment period that is shown as being aligned during a post-adjustment period.

To assist in achieving the alignment, readout 72 during the pre-adjustment period provides any calculated rotation needed of TRUS probe 24 in either a clockwise ("CW") direction or a counterclockwise ("CCW") direction, and any calculated translations needed of grid/template 22 in a X direction and/or a Y direction. Concurrently, readout 73 provides for a current fit error FE1 between tool image 60 and virtual grid 61 ("TGI vs VGI") and/or a current fit error FE2 between EM grid 63 and virtual grid 61 ("EGI vs VGI").

As grid/template 22 and/or probe 24 are being adjusted, readouts 72 and 73 are updated in real-time to assist in achieving the alignment of tool image 60 and virtual grid 61 to the highest degree possible. In practice, readouts 72 and 73 may be color coded to indicate large adjustments/fit errors (e.g., red) and minor adjustments/fit errors (e.g., green).

Also in practice, workstation 40 may provide a warning for adjustments/fit errors exceeding a certain threshold and any offset(s) between tool image 60 and virtual grid 61 may be saved for additional error calculations or corrections (e.g., any rotation of grid/template 22 relative to TRUS probe 24, then a tracking frame of reference can be corrected as needed).

Referring to FIGS. 4-8, those having ordinary skill in the art will appreciate numerous benefits of the present invention including, but not limited to, an optimal grid calibration, particularly for brachytherapy procedures.

Additionally, in practice, embodiments of a workstation of the present invention may be stand-alone workstations or integrated as a software solution into known workstations for performing interventional procedures (e.g., prostate brachytherapy).

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A grid calibration system, comprising:
   interventional equipment including
   at least one interventional tool,
   a grid having a hole matrix for supporting and guiding the at least one interventional tool within a calibration area, and
   an imaging device positioned relative to the grid for generating a tool image that includes at least one flash point illustrative of the at least one interventional tool within the calibration area; and
   a grid calibration workstation in communication with the imaging device (i) to generate a grid calibration image that comprises an overlay of a virtual grid onto the tool image, wherein the virtual grid comprises a point matrix of virtual grid points representative of the hole matrix of the grid, (ii) to calculate at least one calibration adjustment to a relative positioning of the grid and the imaging device, via an image registration, that aligns the at least one flash point of the tool image and a corresponding at least one virtual grid point of the virtual grid, and (iii) to display the at least one calibration adjustment to the relative positioning of the grid and the imaging device.

2. The grid calibration system of claim 1, wherein the at least one calibration adjustment comprises an alignment adjustment that includes a horizontal adjustment of the grid relative to the imaging device.

3. The grid calibration system of claim 1, wherein the at least one calibration adjustment comprises an alignment adjustment that includes a vertical adjustment of the grid relative to the imaging device.

4. The grid calibration system of claim 1, wherein the at least one calibration adjustment comprises an alignment adjustment that includes a rotational adjustment of the imaging device relative to the grid.

5. The grid calibration system of claim 1, wherein the grid calibration workstation is further operable to display an adjustment fit error of the tool image to the virtual grid.

6. The grid calibration system of claim 1,
   wherein a tracking grid is representative of a tracking of at least one of (i) the grid within a tracking coordinate system and (ii) the at least one interventional tool as supported and guided by the grid within the tracking coordinate system; and
   wherein the grid calibration workstation is further operable to display a virtual tracking fit error of the tracking grid to the virtual grid.

7. The grid calibration system of claim 1,
   wherein a tracking grid is representative of a tracking of at least one of (i)the grid within a tracking coordinate system and (ii) the at least one interventional tool as supported and guided by the grid within the tracking coordinate system; and
   wherein the grid calibration workstation is further operable to display an image tracking fit error of the tracking grid to the tool image.

8. The grid calibration system of claim 1, wherein the grid calibration workstation is further operable to display the grid calibration image illustrating the overlay of the virtual grid onto the tool image in real-time.

9. The grid calibration system of claim 8, wherein the image registration includes:
   the grid calibration workstation identifying (i) the at least one flash point illustrative of the at least one interventional tool within the tool image and (ii) the corresponding at least one virtual grid point within the virtual grid; and
   the grid calibration workstation calculating a transformation matrix as a function of each flash point illustrative of the at least one interventional tool identified within the tool image and each virtual grid point identified within the virtual grid.

10. The grid calibration system of claim 1,
    wherein a tracking grid is representative of a tracking of at least one of (i) the grid within a tracking coordinate system and (ii) the at least one interventional tool as supported and guided by the grid within the tracking coordinate system; and
    wherein the grid calibration workstation is further operable to display the grid calibration image illustrating an overlay of the virtual grid and the tracking grid onto the tool image in real-time.

11. The grid calibration system of claim 10, wherein the image registration includes:
    the grid calibration workstation identifying (i)the at least one flash point illustrative of the at least one interventional tool within the tool image, (ii) the corresponding at least one virtual grid point within the virtual grid, and (iii) at least one tracking point within the tracking grid; and
    the grid calibration workstation calculating at least one transformation matrix as a function of each flash point illustrative of the at least one interventional tool identified within the tool image, each virtual grid point identified within the virtual grid, and each tracking point identified with the tracking grid.

12. The grid calibration system of claim 1, wherein the at least one interventional tool includes at least one catheter.

13. The grid calibration system of claim 1, wherein the at least one interventional tool includes at least one needle.

14. The grid calibration system of claim 1, wherein the hole matrix of the grid and the point matrix of the virtual grid are identical.

15. The grid calibration system of claim 1, wherein the imaging device is an ultrasound probe.

* * * * *